United States Patent [19]
Rajasekaran

[11] Patent Number: 5,384,022
[45] Date of Patent: Jan. 24, 1995

[54] METHOD AND APPARATUS FOR ELECTROPHORETIC DNA BAND ISOLATION

[75] Inventor: Ayyappan K. Rajasekaran, New York, N.Y.

[73] Assignee: Cornell Research Foundation, Inc., Ithaca, N.Y.

[21] Appl. No.: 118,045

[22] Filed: Sep. 8, 1993

[51] Int. Cl.$^6$ .............................................. C25B 9/00
[52] U.S. Cl. .............................. 204/299 R; 204/182.8; 204/180.1
[58] Field of Search ............... 204/299 R, 180.1, 182.8

[56] References Cited

U.S. PATENT DOCUMENTS

| | | | |
|---|---|---|---|
| 4,964,961 | 10/1990 | Brautigam et al. | 204/299 R |
| 5,217,591 | 6/1993 | Gombocz et al. | 204/299 R |
| 5,217,593 | 6/1993 | MacConnell | 204/299 R |

OTHER PUBLICATIONS

GeneCAPSULE ™, Copyright 1994, Geno Technology, Inc.

Primary Examiner—John Niebling
Assistant Examiner—C. Delacroix-Muirheid
Attorney, Agent, or Firm—Perman & Green

[57] ABSTRACT

An electrophoresis system is used to segregate a molecular specimen, the apparatus comprising a container, a gel layer and a buffer solution resident in the container, the gel layer having a well for receiving the molecular specimen. Electrical contacts are resident in the container and apply a potential across the gel layer to enable migration of the molecular specimen along a migration path in the gel layer. A second well is positioned in the gel layer and downstream in the migration path. A cup is inserted into the second well, the cup having a rim which, when the cup is resident in the second well, is positioned below the migration path of the molecular specimen within the gel layer. A membrane is also placeable in the second well to prevent migration of the molecular specimen past the cup. The molecular specimen thereby migrates into the cup and is prevented by the membrane from further migration along the migration path. Aspiration of the contents of the cup enables recovery of the molecular specimen.

12 Claims, 2 Drawing Sheets

METHOD AND APPARATUS FOR ELECTROPHORETIC DNA BAND ISOLATION

This invention was made with Government support under Grant No. GM-34107-10, awarded by the National Institutes of Health. The Government has certain rights in the invention.

FIELD OF THE INVENTION

This invention relates to electrophoresis methods and apparatus, and more particularly, to a method and apparatus for enabling improved isolation and extraction of a DNA band from an electrophoretic gel.

BACKGROUND OF THE INVENTION

Electrophoresis is the movement of electrically charged particles that are suspended in a fluid or gel under the influence of an applied electrical field. One of the more routine uses of electrophoretic apparatus is to separate DNA particles into discrete bands for later isolation and recovery. Once a molecular specimen including DNA molecules has been subjected to an electrophoresis procedure, several methods are available for removing a specific DNA band from an electrophoretic gel. A first method involves cutting out the identified DNA band from the gel, dissolving the gel and then precipitating the DNA. A second method involves making a slit into the gel in the direction of migration of a DNA band that is to be segregated. An immobilized support is then inserted into the gel slit and the electric field re-applied across the gel. This causes the DNA band to migrate and bond to the support, which can then be removed to enable elution of the DNA from the support. Each of the aforementioned method requires processing of either the gel or the support to recover the DNA, which processing results in an inevitable loss of some of the DNA.

It is therefore an object of this invention to provide an improved method and apparatus for DNA recovery from an electrophoresis apparatus.

It is another object of this invention to provide an improved apparatus for recovery of a DNA band from an electrophoresis apparatus, which apparatus achieves improved yields of recovered DNA.

SUMMARY OF THE INVENTION

An electrophoresis system is used to segregate a molecular specimen, the apparatus comprising a container, a gel layer and a buffer solution resident in the container, the gel layer having a well for receiving the molecular specimen. Electrical contacts are resident in the container and apply a potential across the gel layer to enable migration of the molecular specimen along a migration path in the gel layer. A second well is positioned in the gel layer and downstream in the migration path. A cup is inserted into the second well, the cup having a rim which, when the cup is resident in the second well, is positioned below the migration path of the molecular specimen within the gel layer. A membrane is also placeable in the second well to prevent migration of the molecular specimen past the cup. The molecular specimen thereby migrates into the cup and is prevented by the membrane from further migration along the migration path. Aspiration of the contents of the cup enables recovery of the molecular specimen.

DETAILED DESCRIPTION OF THE INVENTION

Figure 1:
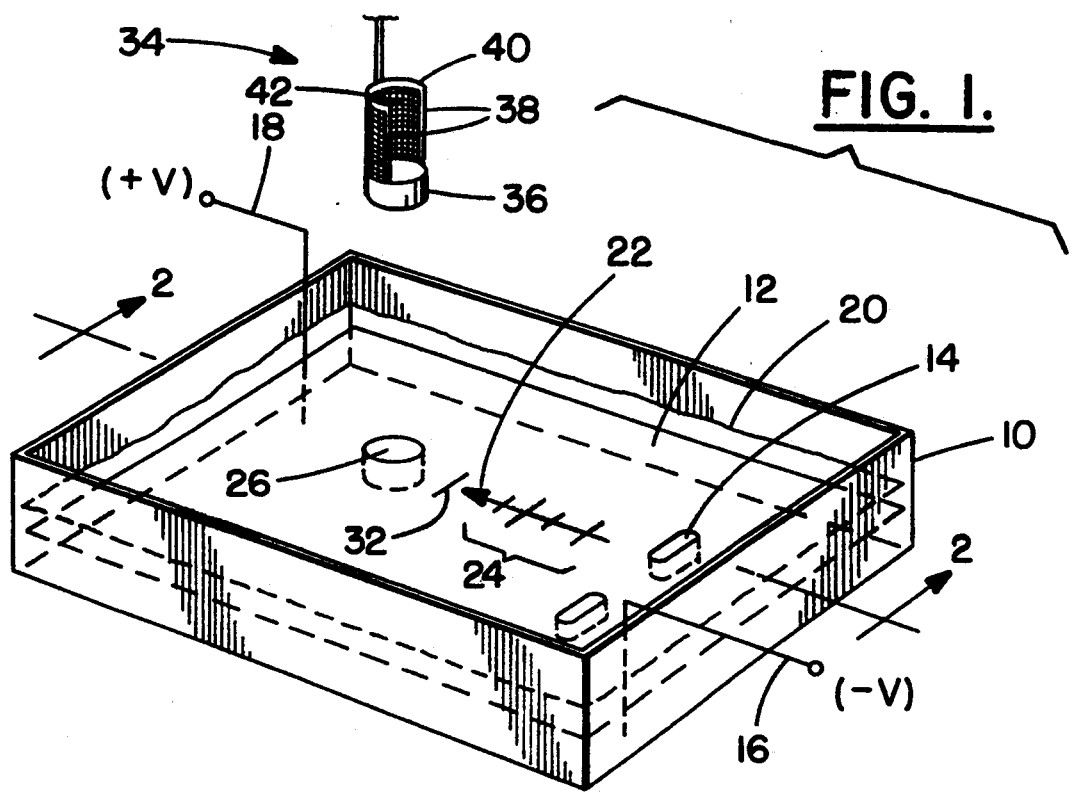
FIG. 1 is a perspective view of an electrophoresis apparatus embodying the invention.
Figure 2:
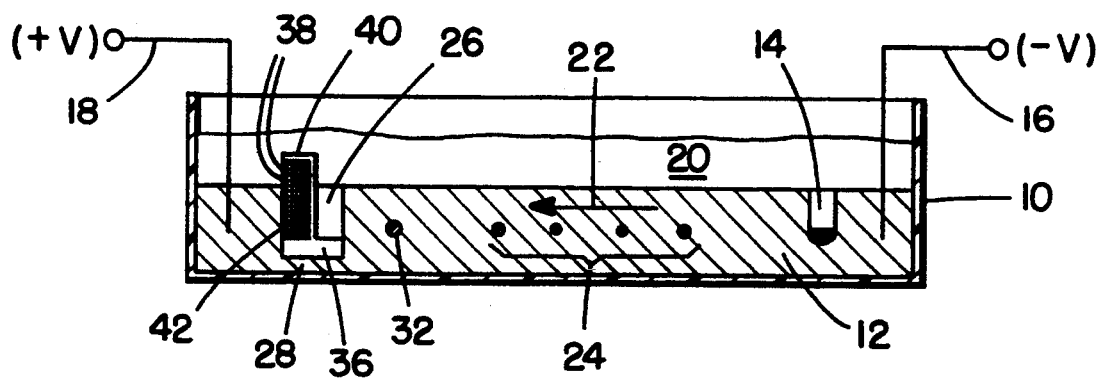
FIG. 2 is a sectional view of the electrophoresis apparatus of FIG. 1 taken along a line 2—2.

Referring to FIGS. 1 and 2, a container 10 includes a gel layer 12 (e.g. agarose) that is provided with a plurality of wells 14 for receiving specimens containing DNA to be segregated. A pair of electrodes 16 and 18 (shown schematically) enable application of an electric field across gel layer 12 to cause electrophoretic migration of DNA species from wells 14. A gel running buffer 20 covers gel layer 12 in the known manner.

To achieve a separation of the DNA within wells 14, an appropriate potential is applied between terminals 16 and 18, and various DNA molecular weights migrate along a migration path (indicated by arrow 22). As is known, various molecular species of DNA migrate at different rates, depending upon their molecular weight and charge. As a result, the DNA molecular species segregate into bands 24 which can then be visualized and/or recovered. Visualization is aided if the gel layer contains ethidium bromide, thereby enabling DNA bands to be visualized under a UV light.

To enable recovery of a DNA molecular species, a well 26 is cut into gel layer 12 just in front of the DNA band to be recovered, taking care that the bottom of well 26 does not extend throughout the thickness of gel layer 12. With reference to FIG. 2, it can be seen that the depth of well 26 ends above the interface between gel layer 12 and container 10. Allowing area 28 of gel layer 12 to remain prevents a distortion of the electric field that would result if well 26 extended to the surface of container 10 and allowed buffer 20 to make contact therewith. Well 26 may be made by any suitable cutter that enables a plug of gel layer 12 to be removed.

Figure 3:
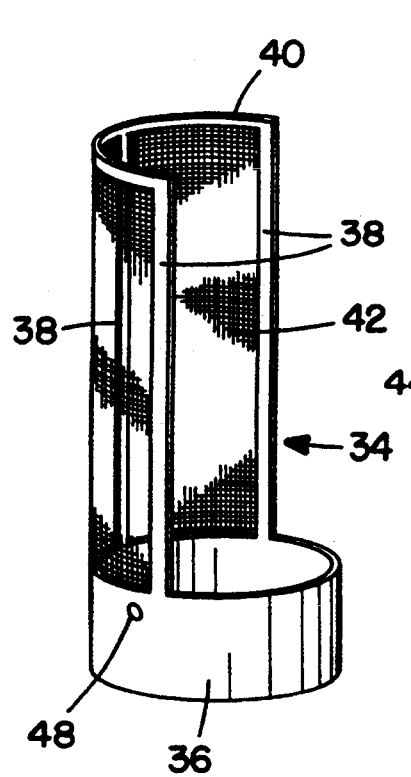
FIG. 3 is a perspective view of a DNA collection cup employed with the invention.

Once well 26 is positioned downstream from a DNA band to be recovered (e.g., band 32), a DNA collection cup assembly 34 is inserted into well 26. Cup assembly 34 is shown in greater detail in FIG. 3 and comprises a cup portion 36 from which extends a plurality of vertical struts 38. At least the bottom-most surface of cup portion 36 should be transparent so that DNA collected in the cup portion can be visualized from below when the contents are illuminated by a UV light source.

The uppermost portions of each of struts 38 are connected by a semi-circular strut 40 which provides structural integrity to the assembly. A membrane 42 is stretched over and adheres to struts 38 and creates a semi-cylindrical shape above cup portion 36. Membrane 42 is selected so that it is water permeable, but is impermeable to larger sized molecules, such as the molecules of the DNA band that are to be recovered. Preferably, membrane 42 is comprised of a dialysis membrane of the type employed in dialysis equipment. Such membranes can be obtained from Spectrum Medical Industries Inc., 60916 Terminal Annex, Los Angeles, Calif. 90060.

Figure 4:
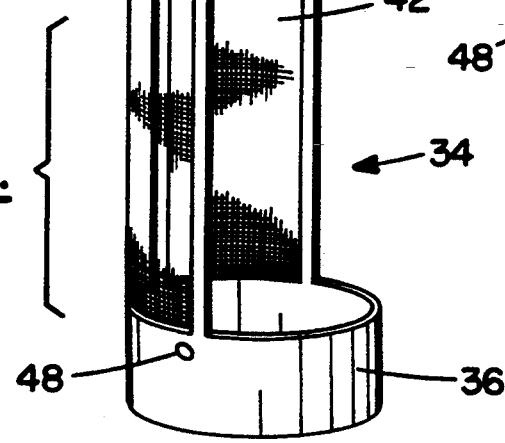
FIG. 4 is a perspective view of the DNA collection cup of FIG. 3 with a protection flap disposed thereover.
Figure 5:
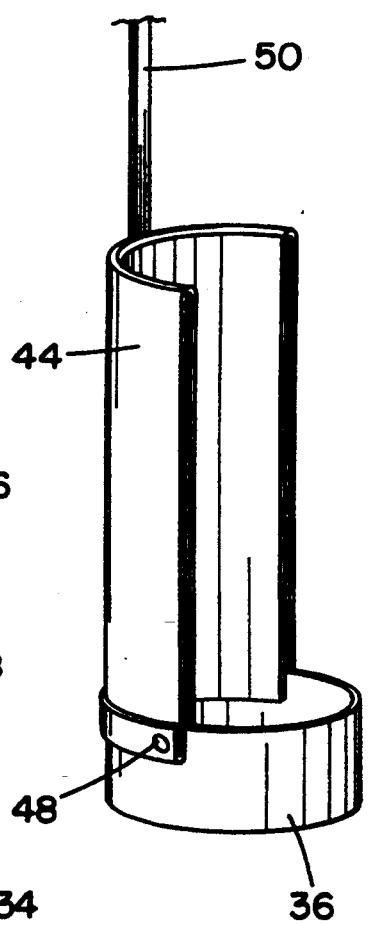
FIG. 5 is a view of the DNA collection cup of FIG. 3 with the protection flap in place.

Because dialysis membrane 42 is fragile, it is protected prior to insertion of cup assembly 34 into well 26. The protection is illustrated in FIG. 4 and is provided by a flap 44 that is positioned to slide over struts 38, 40 and membrane 42. A pair of holes 46 on the lower most extremity of flap 44 engage rounded extensions 48 from cup portion 36, thereby maintaining flap 44 in place when it is positioned as shown in FIG. 5. A handle 50 enables flap 44 to be pulled upwardly (disengaging holes 46 and extensions 48), once DNA cup assembly 34 has been emplaced in well 26. Flap 44 should have sufficient structural rigidity to enable pressure on handle 50 to insert cup assembly 34 into well 26.

DNA collection cup assembly 34 is preferably comprised of a molded plastic, with dialysis membrane 32 bonded to its exterior surface about struts 38 and 40. The diameter of cup portion 36 is preferably substantially identical to that of well 26 so that there is little or no gap between itself and the walls of well 26 when DNA collection cup assembly 34 is inserted thereinto. Those skilled in the art will realize that while DNA collection cup assembly 34 is shown as a single assembly, that struts 38, 40 and dialysis membrane 42 may be made separately from cup portion 36. Further, the upper rim of cup portion 36, when positioned within well 26 should lie below the position of band 32 within gel layer 12. This enables band 32, when exiting a wall of well 26 under the influence of the electric field, to be completely collected within cup portion 36.

Returning to FIGS. 1 and 2, if it is assumed that a molecular DNA specimen has been placed in well 14 and that electrophoretic separation has taken place such that bands 24 and 32 are now positioned within gel layer 12, the DNA particles within band 32 may now be collected. This is accomplished by removing buffer solution 20 and excising a cylindrical portion of gel layer 12 that is immediately downstream from band 32 (in the direction of band migration). DNA collection cup assembly 34 is then emplaced into well 26 and flap 44 is removed. A volume of gel running buffer 20 is then added to container 10 to form a thin layer over gel layer 12. Voltage is then re-applied across electrodes 16 and 18, and the electrophoresis action recommences. As a result, band 32 moves to the left (in the Figures) and into buffer 20 that is present within well 26.

Electrophoresis membrane 42 prevents any of the DNA particles within band 32 (and in well 26) from continuing to migrate along gel layer 12, even though water and current are enabled to flow therethrough. Once the DNA within band 32 has been captured in cup portion 36, power is removed from electrodes 16 and 18. The gel is then exposed to a UV light source to enable confirmation that the DNA band is present in cup portion 36. The solution of DNA may then be aspirated from cup portion 36, precipitated and used for further studies.

Figure 6:
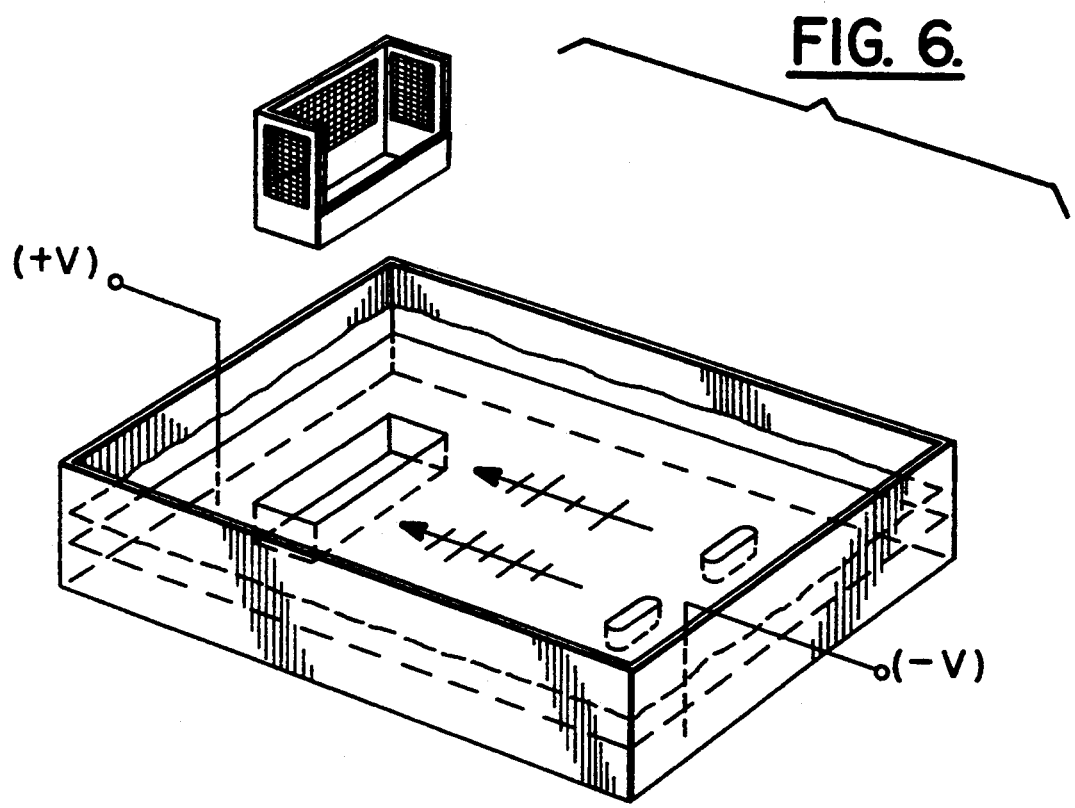
FIG. 6 is a perspective view of the apparatus of FIG. 1 wherein a collection cup spans several electrophoretic migration paths.

It should be understood that the foregoing description is only illustrative of the invention. Various alternatives and modifications can be devised by those skilled in the art without departing from the invention. For example, the size and shape of cup portion 36 may be varied in accordance with the amount of DNA to be collected. Thus, where a large amount of DNA is to be prepared and multiple sample wells are employed, cup portion 36 will be of a size and shape to extend over multiple DNA migration paths extending from the multiple sample wells (see FIG. 6). When two closely migrating DNA bands are to be purified, the shape and the capacity of the cup will be made different so that it can be placed in between the two closely migrating DNA bands (for example, DNA bands migrating a few millimeters (3-5 mm) away from each other). Accordingly, the present invention is intended to embrace all such alternatives, modifications and variances which fall within the scope of the appended claims.

I claim:

1. Electrophoretic apparatus for segregating a molecular species, said apparatus comprising:
   a container;
   a gel layer and buffer solution resident in said container, said gel layer having a first well for receiving said molecular species;
   electrical means for applying a potential to said gel layer to cause migration of said molecular species from said first well and along a migration path in said gel layer;
   a second well in said gel layer, said second well positioned in said migration path;
   cup means for insertion in said second well, said cup means having a rim which, when said cup means is resident in said second well, is positioned below said migration path of said molecular species in said gel layer; and
   membrane means placeable in said second well to prevent migration of said molecular species past said cup means along said migration path, whereby electrophoretic migration causes said molecular species to enter said second well and to be collected within said cup means for later recovery.

2. The electrophoretic apparatus as recited in claim 1, wherein said membrane means comprises a dialysis membrane that is substantially impervious to said molecular species.

3. The electrophoretic apparatus as recited in claim 1, wherein said cup means and membrane means comprise unitary assembly.

4. The electrophoretic apparatus as recited in claim 3, wherein said cup means is a concave cup having a rim with a circumference that approximates a circumference of said second well, said rim provided with plural vertical struts for supporting said membrane means.

5. The electrophoretic apparatus as recited in claim 4, wherein said struts are positioned about said circumference of said rim to enable said membrane means to achieve a concave shape about a portion of said rim and to extend upwardly from said rim, said concave shape extending across said migration path to create an impediment to passage of said molecular species.

6. The electrophoretic apparatus as recited in claim 5, wherein said membrane means is a dialysis membrane that is substantially impervious to said molecular species.

7. The electrophoretic apparatus as recited in claim 6, further comprising a protective flap which encompasses said dialysis membrane and strut and is slidably engagable with said cup portion, said protective flap enabling insertion of said unitary assembly into said second well without damage to said dialysis membrane.

8. The electrophoretic apparatus as recited in claim 1, wherein said second well has a depth that does not penetrate an entire thickness of said gel layer.

9. The electrophoretic apparatus as recited in claim 1, wherein said apparatus includes a plurality of first wells, said second well spanning migration paths from each of said first wells, said cup means shaped to also span said migration paths.

10. A DNA collection cup for use with a gel electrophoresis apparatus, said DNA collection cup comprising:
  a concave cup having a rim;
  a plurality of struts upwardly extending from said rim, said struts connected at their uppermost points by an additional strut, at least a pair of said upwardly extending struts positioned at opposite sides of said rim; and
  a dialysis membrane extending from one upwardly extending strut, along said rim of said cup portion, to another upwardly extending strut and from said rim to said additional strut so as to create an open-faced barrier to electrophoresed DNA particles to be collected in said cup portion.

11. A method for segregating molecular species, said method employing electrophoresis apparatus comprising a container, a gel in said container having at least one well for said molecular species and means for applying a separation potential to said gel to enable migration of said molecular species along a migration path, said method comprising the step of:
  a. creating a well in said gel in said migration path of said molecular species;
  b. emplacing in said well a collection cup and a molecular species blocking membrane that substantially prevents passage of said molecular species past said collection cup, said membrane positioned across said migration path;
  c. operating said electrophoretic apparatus to cause said molecular species to move along said migration path, into said well and into said collection cup, said membrane restricting further migration of said molecular species along said migration path; and
  d. recovering said molecular species from said cup.

12. The method as recited in claim 11 wherein said well that is created in step (a) does not extend through an entire thickness of said gel, but rather leaves a layer of gel between a bottom of said collection cup and a portion of said container that resides therebeneath, said well, nevertheless having sufficient depth to place a rim of said collection cup beneath said migration path so as to enable substantially all of said molecular species to enter therein upon electrophoretic migration.

* * * * *